US010215735B1

(12) United States Patent
Ziola et al.

(10) Patent No.: US 10,215,735 B1
(45) Date of Patent: Feb. 26, 2019

(54) TREATMENT METHOD FOR SERVICE LIFE EXTENSION OF PRESSURE VESSELS

(71) Applicant: Digital Wave Corporation, Centennial, CO (US)

(72) Inventors: Steven M. Ziola, Centennial, CO (US); Brian M. Burks, Centennial, CO (US); Michael R. Gorman, Centennial, CO (US)

(73) Assignee: Digital Wave Corporation, Cenennial, CO (US)

( * ) Notice: Subject to any disclaimer, the term of this patent is extended or adjusted under 35 U.S.C. 154(b) by 109 days.

(21) Appl. No.: 15/188,979

(22) Filed: Jun. 21, 2016

(51) Int. Cl.
*G01N 29/14* (2006.01)
*G01N 29/04* (2006.01)

(52) U.S. Cl.
CPC .............. *G01N 29/14* (2013.01); *G01N 29/04* (2013.01)

(58) Field of Classification Search
CPC .............................. G01N 29/04; G01N 29/14
See application file for complete search history.

(56) References Cited

U.S. PATENT DOCUMENTS

| | | | | |
|---|---|---|---|---|
| 4,009,463 A | * | 2/1977 | Vercellotti | G01N 29/14 367/127 |
| 4,468,965 A | * | 9/1984 | Blackburn | G01N 29/14 73/587 |
| 4,577,487 A | * | 3/1986 | Dooley | G01N 29/227 73/37 |
| 4,641,526 A | * | 2/1987 | Izumi | G01S 5/18 367/124 |
| 4,732,045 A | * | 3/1988 | Blackburn | G01N 29/14 73/37 |
| 5,554,810 A | * | 9/1996 | Anifrani | G01N 29/14 73/587 |
| 5,861,548 A | * | 1/1999 | Melvin, II | G01L 11/04 73/49.3 |
| 5,929,315 A | * | 7/1999 | Dunegan | G01H 1/00 73/1.82 |
| 6,041,656 A | * | 3/2000 | Dunegan | G01H 1/00 73/587 |
| 6,360,608 B1 | * | 3/2002 | Dunegan | G01H 1/00 73/587 |

(Continued)

OTHER PUBLICATIONS

Burks et al., "Fatigue life improvement of DOT-CFFC composite cylinders," Dec. 2015, Digital Wave, 151 pages.*

*Primary Examiner* — John Fitzgerald
(74) *Attorney, Agent, or Firm* — Furman IP Law

(57) ABSTRACT

Provided herein are systems and methods for achieving an extended service life for a pressure vessel that has experienced a prior service life. In some embodiments, the service life of the vessel has expired. The service vessel has an unknown damage condition, including defects sustained during the service life. Despite these defects and unknown accumulated damage state, the embodiments described herein may be used to test these vessels, to safely pressurize the vessels beyond pressures deemed safe for the vessel to experience in its damaged state, and to recommission a new service life for the vessel. The recommissioning of the vessel for an additional service interval may include meeting certain requirements for the pressure vessel, and embodiments described herein include exemplary measurements and observations to assure these requirements of the rejuvenated vessel are met.

17 Claims, 11 Drawing Sheets

(56) References Cited

U.S. PATENT DOCUMENTS

| | | | | |
|---|---|---|---|---|
| 6,628,567 B1* | 9/2003 | Prosser | ............... | G01H 1/00 |
| | | | | 367/13 |
| 7,698,943 B2* | 4/2010 | Bohse | ............... | G01N 29/14 |
| | | | | 702/82 |
| 8,240,209 B2* | 8/2012 | Murakami | ......... | G01N 29/043 |
| | | | | 73/587 |
| 2007/0113959 A1* | 5/2007 | Minta | ............... | F17C 1/002 |
| | | | | 156/184 |
| 2008/0148853 A1* | 6/2008 | Kim | ............... | F17C 13/02 |
| | | | | 73/587 |
| 2008/0302186 A1* | 12/2008 | Bohse | ............... | G01N 29/14 |
| | | | | 73/587 |
| 2010/0107765 A1* | 5/2010 | Murakami | ......... | G01N 29/043 |
| | | | | 73/587 |
| 2016/0214328 A1* | 7/2016 | MacAdams | ............ | C09J 5/02 |
| 2016/0356419 A1* | 12/2016 | Christ | ............... | B29C 70/32 |
| 2016/0377228 A1* | 12/2016 | Fratti | ............... | F17C 1/00 |
| | | | | 53/433 |

\* cited by examiner

US 10,215,735 B1

TREATMENT METHOD FOR SERVICE LIFE EXTENSION OF PRESSURE VESSELS

FIELD OF THE TECHNOLOGY

The present disclosure relates to pressure vessels with at least one layer of composite material and at least one metallic layer.

SUMMARY OF THE DESCRIPTION

Provided herein are systems and methods for achieving an extended service life for a pressure vessel that has experienced a prior service life. In some embodiments, the service life of the vessel has expired. The service vessel has an unknown damage condition, including defects sustained during the service life. Despite these defects and unknown accumulated damage state, the embodiments described herein may be used to test these vessels, to safely pressurize the vessels beyond pressures deemed safe for the vessel to experience in its damaged state, and to recommission a new service life for the vessel. The recommissioning of the vessel for an additional service interval may include meeting certain requirements for the pressure vessel, and embodiments described herein include exemplary measurements and observations to assure these requirements of the rejuvenated vessel are met.

In one aspect, the disclosure describes a method of rejuvenating a pressure vessel including receiving a pressure vessel including at least one composite layer and a metallic layer after the pressure vessel has accumulated a plurality of defects in the metallic layer during a first service interval, and the pressure vessel having a test pressure. The method then proceeds by increasing an internal pressure of the pressure vessel and in response to increasing the internal pressure of the pressure vessel, receiving first information about the at least one composite layer. The method further includes first determining from the first information that increasing the internal pressure of the vessel to an autofrettage pressure of the vessel that is above the test pressure of the vessel will not damage the vessel enough as to cause the vessel to fail to receive approval for an additional service interval. The method further includes, based on the first determining, continuing the increasing of the internal pressure to an autofrettage pressure that is adapted to plastically strain portions of the metallic layer that are adjacent to each of the plurality of defects. The method further comprises, after increasing the internal pressure of the pressure vessel to the autofrettage pressure, decreasing the internal pressure of the pressure vessel and, based on decreasing the internal pressure of the pressure vessel, receiving second information about the at least one composite layer. The method further includes, based on the first information and the second information, second determining that the pressure vessel may be returned to service for the additional service interval.

Other embodiments and features of the present disclosure will be apparent from the accompanying drawings and from the detailed description which follows.

BRIEF DESCRIPTION OF THE DRAWINGS

The embodiments are illustrated by way of example and not limitation in the Figures of the accompanying drawings in which like references indicate similar elements.

DESCRIPTION

The following patent description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

Figure 1:
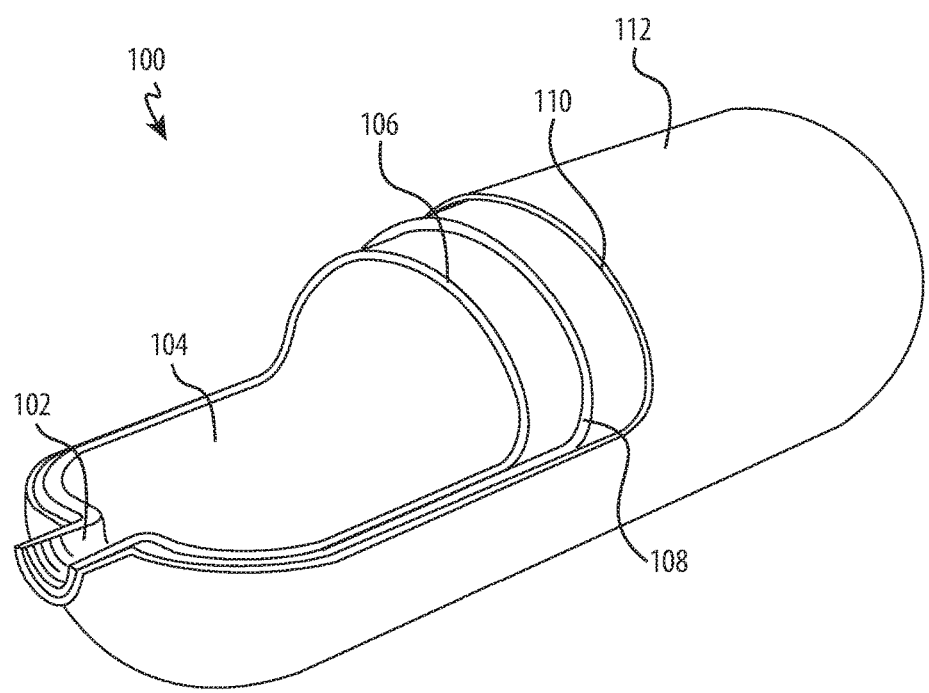
FIG. 1 shows an opened view of the construction of an exemplary pressure vessel containing a metallic layer and a composite layer in the form of a cylinder.

FIG. 1 shows an opened view of the construction of an exemplary pressure vessel containing a metallic layer and a composite layer in the form of a cylinder. The cylinder is constructed with an internal metallic layer 106 for containing the pressure inside the vessel and a composite outer structure 108 supporting the metallic layer (e.g., a carbon fiber epoxy matrix). As described further herein the composite outer structure 108 may include one or more composite layer(s).

These vessels have been designed to contain pressure within the metallic layer 106 while the forces on the metallic layer in resisting this pressure are taken by the surrounding composite structure. The metallic layer 106 is commonly manufactured from aluminum, which may be very thin and fatigue failure of this layer is described further in greater detail as a failure mechanism for these vessels. The composite layers 108 may be constructed of carbon fibers suspended in epoxy or some other composite material. In addition, the vessel may include a polymer or other surface layer 110, such as an environmental barrier at the outer surface of the vessel 112 to protect the composite layer 108 from exposure.

The neck portion of the vessel 102 normally includes significantly more metal for the fitting that then other portions of the metallic layer to provide a solid interface (e.g., metallic threads) for the pressure vessel. The composite layer(s) 108 normally do not engage with the vessel's interface. The other portions of the metallic layer 106 may be significantly thinned, relying instead on the reinforcement of the composite layer 108.

Apart from the neck portion 102, the vessel shown 100 has a generally cylindrical shape, however not all embodiments of a pressure vessel are cylindrical. For example, some pressure vessels are constructed as spheres. Different composite layering or wrapping methods may be used for different vessel shapes. However, despite differences in composite construction, the methods described herein include methods adaptable or useful without adaptation for different vessel shapes.

In many embodiments, a single composite layer 108 does not completely surround the composite pressure vessel 100. In some embodiments, a first composite layer completely covers a portion of the composite vessel and a second composite layer (or combination of layers) covers the remaining portion of the composite vessel 100. In some embodiments, one or more composite layers 108 will completely surround the vessel. In some embodiments, the composite layer 108 completely surrounds the vessel in that it covers the entire surface of a vessel 100, except for a surface portion interfacing with a port or neck portion 102 of the vessel.

In many embodiments, a pressure vessel will be approved for service by a regulatory agency that regulates the pressure vessels (e.g., The U.S. Department of Transportation or DOT). For example, the DOT regulates carbon-reinforced aluminum-lined cylinders (DOT-CFFC) such as the embodiment shown. A regulatory agency may approve a vessel for initial service life and for re-certification at intervals (e.g., service intervals) for continued use during a service life. These approvals may require particular thresholds and specifications to be met before a vessel is allowed by the agency to enter into service. For example, the regulatory agency may approve a vessel for service based on certain life parameters that are determinable by design specification and/or measureable at the time of manufacture.

A regulatory agency may define certain pressures, such as operational pressures, maximum pressures, and/or minimum pressures for normal operation and/or for failure of the vessel. For example, a vessel may have a service pressure (e.g., 4500 psi). From this pressure, a "fast-fill" service pressure may be also be calculated or determined based on the heat created (e.g., with a compressible fluid) and the maximum pressure developed within the vessel while it is filled quickly. In some embodiments, the fast-fill service pressure is the maximum pressure (e.g., 5192 psi) developed while pressurizing the vessel enough that the vessel retains the service pressure (e.g., 4500 psi) after the vessel and contents both cool. As another example, a vessel may have an as-manufactured minimum burst pressure (e.g., 15,300 psi), a pressure which the vessel must be able to withstand without bursting at the time of manufacture.

Similarly, the regulatory agency may define service life periods that must be met by the vessel to receive certification for service. These service life periods may be defined as a number of service pressure cycles (or fast-fill pressure cycles). The vessel may be designed to achieve a certain number of cycles before the metallic layer fails (leaks, cracks, or ruptures). The metallic layer can fail due to defects in the metallic layer (e.g., surface wear, scratches, cracks) that grow in size (e.g., depth) during repeated service cycles. The defects grow through the layer causing the metallic layer to fail eventually. The service life, therefore, is related to the number of cycles that can be subjected to a plurality of defects in the metallic layer before this failure occurs.

Many of these parameters can be simulated during the design phase, achieving a strongly optimized vessel design that provides the required performance for a minimum design cost. However, these designed parameters and simulations are also subject to testing at the time of manufacture. Specifically, statistically selected newly-manufactured vessels are subjected to testing, such as burst testing and/or using tests to simulate years of service life on a sample of vessels selected from a production lines. These types of testing on these vessels most often causes the erstwhile newly-manufactured vessels to never be commissioned for a service life.

In sharp contrast, the processes described further herein for extending the service life (e.g., creating a new service interval after the end of a first service life) of actual vessels with accumulated wear from a service life, such as a plurality of defects, and requires fundamentally different techniques to determine whether the vessels, may be returned to service life after treatment. To be clear, the process of extending a service life for a vessel includes taking a vessel that is no longer approved for service pressures (e.g., decommissioned from use) and proving the recommissioned vessel will meet the requirements for newly-manufactured vessels, such as achieving a service life of the vessel at the service pressure (or fast fill pressure) for a number of cycles, withstanding periodic test pressurizations to a test pressure during recertification, and achieving the same or similar minimum burst pressure as required of newly manufactured vessels.

An entire service life of the pressure vessel may include periodic recertifications of the pressure vessel after a portion of the service life, or a service interval, has completed. For example, after 5 years of service life, regulatory requirements may cause the vessel to be recertified before entering another service interval in the service life of the vessel. This recertification can include testing of the vessel, such as inspecting and pressurizing the vessel, including to an elevated pressure, such as a test pressure that is only approved to be used during the testing for recertification of the vessel. For example, testing may include taking the vessel being recertified to 167% of the service pressure of the vessel.

For many DOT-approved CFFC composite pressure vessels, recertification must occur every five years and include a test pressurization cycle to a test pressure for the vessel. In some embodiments, under DOT regulations, only two recertifications are required during a service life for a vessel, allowing a total of three service intervals before the vessel's complete 15-year service life has expired. After the service life is complete, the DOT does not allow pressurizing of the vessel.

The length and service conditions of the service intervals between recertification of the vessel, as well as the length of the vessel's overall service life, determines the level of damage sustained by the vessel at the end of the vessel's service life. This damage includes a plurality of defects in the metallic layer as well as possible damage to the composite outer layers of the vessel. The composite layers may be damaged from environmental factors of the service. Any of these damages can weaken the pressure vessel, risking failure if service is continued with the vessel.

The regulatory agency's desire to regulate the safety of the vessels mandates that the vessels only be put into service if the intended new service life can be assured to be safe. However, because damage already exists in a vessel that has an expired service life, proving that the vessel can return to service requires significant testing and monitoring to allow additional service by the vessel. Embodiments of methods for rejuvenating a vessel are described herein that allow the return of previously used vessels with accumulated damage to be recommissioned for a new service life or service life interval. Included in this description herein are the results of service life fatigue testing and burst testing on rejuvenated cylinders to confirm that the methods described herein actually extend service life of pressure vessels within the requirements of regulatory agencies, like the DOT.

Figure 2:
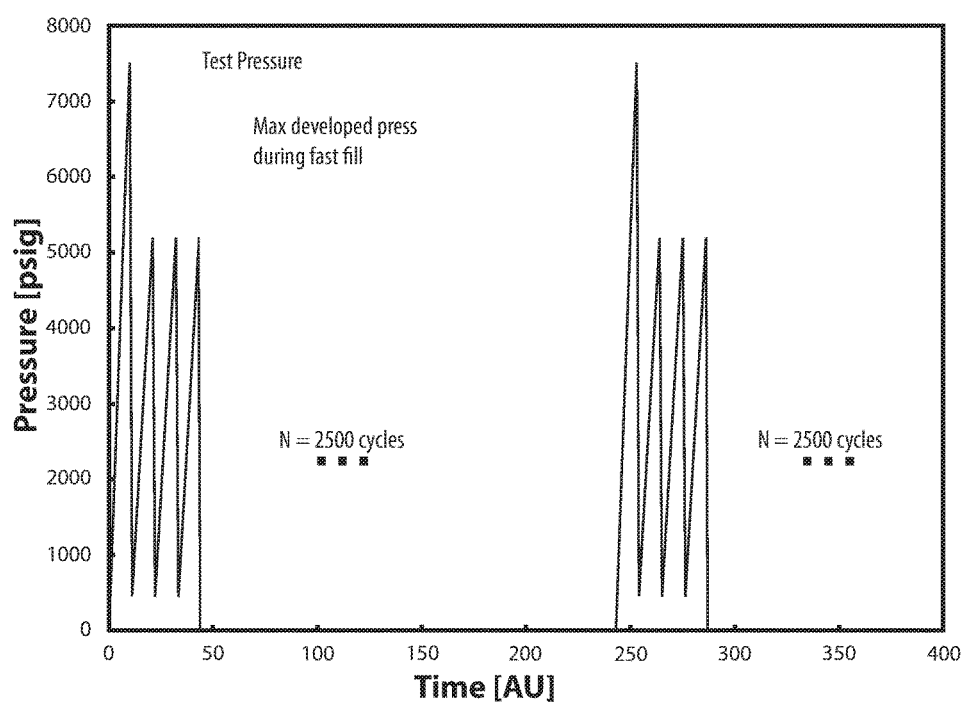
FIG. 2 shows testing of a simulated extended service life using fatigue testing, including cycling to a maximum developed service pressure (e.g., a fast fill pressure) and periodically, cycling up to test pressure.

FIG. 2 shows testing of a simulated extended service life using fatigue testing, including cycling to a maximum developed service pressure (e.g., a fast fill pressure) and periodically, cycling up to test pressure. Shown herein is an exemplary embodiment of a test DOT-CFFC certified cylinder vessel pressurized to a fast fill pressure (e.g., 5192 psi) over a service pressure (e.g., 4500 psi) replicating the effects of filling the cylinder quickly. The vessel is also loaded with a test pressure cycle (e.g., 7500 psi) after every 2,500 service pressure cycles.

This fatigue testing simulates actual service intervals through the period of a service life for a vessel, including the test pressurization cycles at simulated recertification intervals (e.g., after 5 years of simulated service use, or 2,500 fast-fill pressurization cycles). This fatigue testing is also used on vessels treated by the recommissioning processes herein to prove the ability of such vessels to have extended safe service life to the satisfaction of regulatory agencies, such as the U.S. DOT.

Fatigue testing allows for certification for reentry into service, such as described for rejuvenation processing to create a second service life for a vessel after an initial service life is completed. For example, fatigue testing can show the likelihood of failure of a vessel upon return to real world service. As another example, also further described herein, periodically rejuvenated vessels can be shown via fatigue testing to achieve a theoretical indefinite service life. The theoretical indefinite service life can be defined by a standard setting or certifying body (e.g., the Department of Transportation). For example, a threshold for DOT-CFFC pressure vessels may be defined as a threshold of withstanding of 24,000 block loaded service pressure cycles up to a fast fill pressure (e.g., 5192 psi) and loaded with a test pressure cycle (e.g., 7500 psi) after every 2,500 service pressure cycles. Such a test program has been run, in which it was found that the vessels maintained a characteristic damage state after processing that allows rejuvenated vessels to be recommissioned safely for a new service life.

In addition to proving fatigue performance after the using the described processing methods, the recommissioned vessels have been shown consistently to attain the minimum burst pressure during end of life testing. This is true for both vessels that were burst tested directly after treatments described herein (satisfactory performance at beginning of recommissioned life) and after fatigue testing to 15,000 or more cycles.

As described further herein, the unknown service history of a vessel further complicates the processes for extending the service life of the vessels received at the end of their service life. For example, fire may create damage to the composite layers. As another example, scratches, corrosion, or other defects may be created in any part of the vessel by the physical environments of the service life. As yet another example, surface wear, pitting, cracks, corrosion, or other defects in the metallic layer may accumulate during the expired service life of a vessel as received into the described processes. As described herein, monitoring the vessel during certain portions of the processing can be used to determine indications of a vessel's ability to withstand the processing described herein, and to successfully receive an extended service life. These monitoring processes are described further herein, along with the indications considered when determining whether the process of extending the service life can complete successfully.

A vessel may have received damage during manufacture or during its completed service life. For example, sources of damage include normal or abnormal use and environmental exposure during its service life, as well as unknown manufacturing history, including design and initial manufacturing processes, such as an autofrettage cycle plasticizing portions of the newly-manufactured metallic layer. In different embodiments described herein, the rejuvenating processes include each of these possibilities. For example, embodiments are described herein for taking a vessel to the autofrettage pressure(s) while the vessel has accumulated damage (e.g., hard water or fire exposure) and a significant unknown service history (e.g., an expired service life of 15 years, after three service intervals of 5 years each).

Damage to the metallic layer and composite layers can come from service use and environmental causes. However, as described herein, this damage state may not be known or may be only partially known. As used herein, therefore, the term defect used with respect to the metallic layer includes damage to the metallic layer from environmental conditions, surface wear, pitting, cracks, and scratches in the metallic layer. Damage to the composite layer may be generally referred to herein or may be specified with respect to the type of damage caused, such as fiber breakages or delaminations in the composite layer(s).

Figure 3:
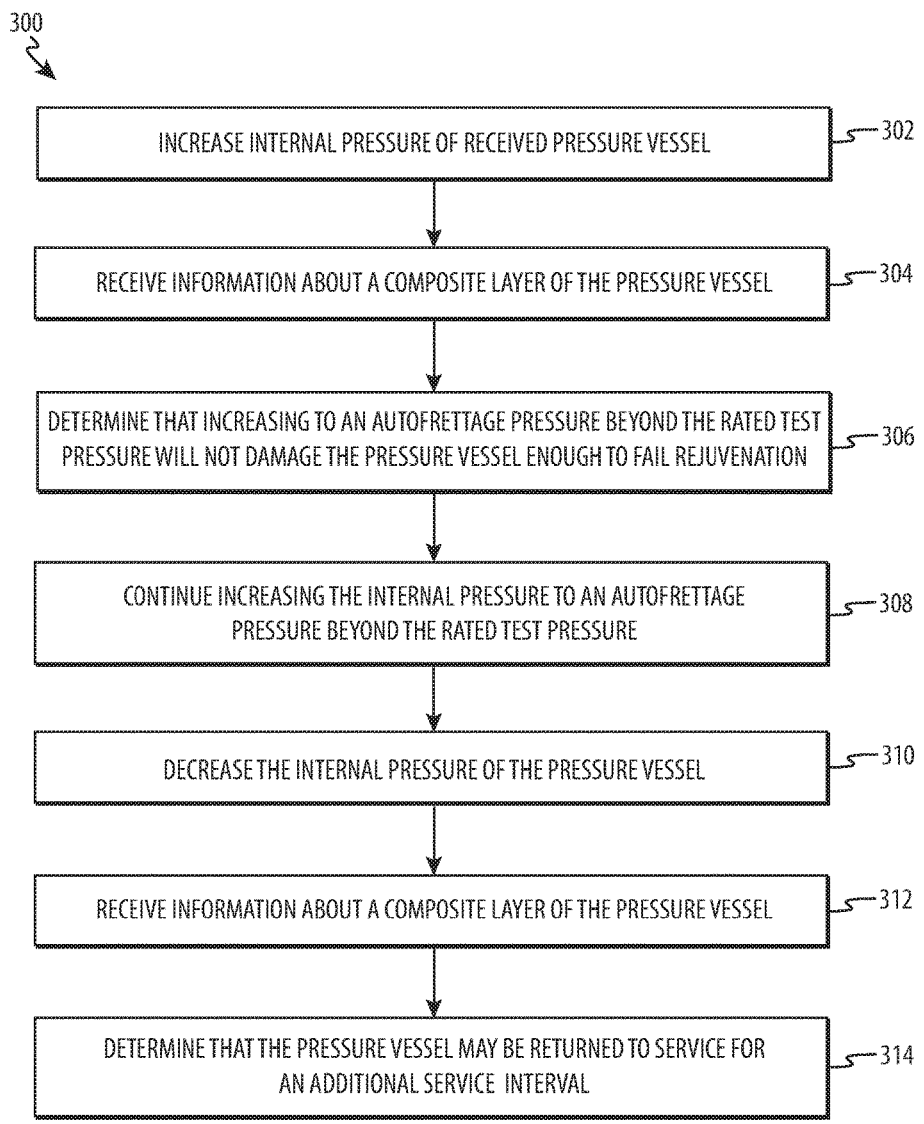
FIG. 3 shows a flow chart for extending the service life of a vessel that is received with an unknown service history via a rejuvenation process.

FIG. 3 shows a flow chart for extending the service life of a vessel that is received with an unknown service history via a rejuvenation process. The term rejuvenation process as used herein includes a re-autofrettage processing of a service-expired vessel, with various embodiments described in greater detail herein. Because the entire process 300 culminates in determining to extend the service life of a previously-retired vessel, the process it is described herein as a rejuvenation process.

The rejuvenation process 300 begins by receiving a pressure vessel that includes at least one composite layer and a metallic layer, particularly as shown in FIG. 1 with the at least one composite layer supporting the metallic layer. The pressure vessel is received with an unknown degree and nature of accumulated damage, such as a plurality of defects in the metallic layer, or damage to the one or more composite layers.

The method 300 includes increasing 302 an internal pressure of the received pressure vessel that has been received after a service life has been expired. In one embodiment, increasing 302 an internal pressure can include pressurizing a portion of the pressure vessel separately from another portion of the pressure vessel, if such separate pressurizing is possible in the pressure vessel. As described herein there is a single internal pressure available to be pressurized in the pressure vessel and that internal pressure is supported by the combination of the metallic layer and the one or more composite layers.

The term increasing the internal pressure 302 describes increasing the internal pressure over an ambient pressure experienced by the vessel in the other side of the one or more composite layers. As commonly constructed, the one or more composite layers is contacted by, covered by, or suspended in an epoxy or other rigid or stiff polymer layer. The ambient pressure may be experienced by the vessel through a polymer layer, complete or incomplete, or surface covers, such as decals or other coverings.

The method includes receiving information about the composite layer of the pressure vessel 304. Information may be received from the pressure vessel during any part of the process 300, such as during the process of pressurizing the vessel, changing the pressure, and/or holding the pressure constant. In one embodiment, the information received about the vessel is specifically originating from the one or more composite layers and may be monitored. In other embodiments this information received about the vessel also includes information about other portions of the vessel. For example, physical (e.g., strain gauges), visual or other measurements of the vessel may include information about the metallic layer or other portions of the vessel.

In one embodiment, the information received 304 is acoustic information that is generated by the vessel in response to increasing the internal pressure of the vessel. In several embodiments, information may be received (e.g., 312) during another phase of the process 300 (e.g., in response to that phase of the process) and used for different determinations about the vessel and its rejuvenation. Additional information may be used about the vessel, such as a service history (e.g., environmental exposure) that could further aid the rejuvenation processing 300, but in many embodiments no such information is used or assumed except as explicitly mentioned in the processes described herein.

The unknown accumulated damage may create different information received 304, allowing the process to determine the extent to which the damage exists and/or whether the vessel can successfully complete the rejuvenation process 300. For example, as described further herein, certain information can be used to determine (e.g., 306, 314) whether a pressure vessel will be able to withstand a certain pressure (e.g., test pressure, autofrettage pressure, minimum burst pressure) or whether the pressure vessel may be safely granted an additional service life.

In some embodiments, the information is received 304 directly from sensors in contact with the vessel. In other embodiments, information may be received 304 directly from visual inspection of the vessel. In other embodiments, information may be received 304 about a vessel that is undergoing remote monitoring or monitoring at a distance, including information received that is transmitted, delayed, stored, or otherwise processed before being received. The information may include acoustic information that is ultrasonic, and detectable only via sensor that has detection beyond that of the natural human ear. For example, the acoustic information may include modal acoustic emission (MAE) and this acoustic information may be processed, filtered, and/or stored before or after receiving 304 the information.

The rejuvenation process 300 includes both determining 306 that the vessel can continue increasing pressure (e.g., to a test pressure, to an autofrettage pressure) as well as determining 314 that the service life should be extended for the vessel being processed. The various damage thresholds for making these determinations to continue 306 and/or grant additional service are described in further detail herein. The determinations 306 and 314 may use similar or the same information. For example, modal acoustic emission information that is used to calculate a likely future burst pressure may be used to determine whether the vessel may be granted an additional service interval. Being able to withstand the required burst pressure is an important threshold for determining whether to continue the rejuvenation process 300 with the possibility of successfully completing the process with a determination 314 that the vessel may be returned to service for an extended service life.

The rejuvenation process 300 uses the information received in 304 to determine 306 whether increasing the internal pressure of the vessel above the rated test pressure for the vessel would not cause the vessel to accumulate further damage so as to make the vessel unusable. For example, this determining step 306 that the continuing the rejuvenation process to the end will not damage the vessel allows the rejuvenation process 300 to be stopped early for a vessel that has accumulated too much damage to be rejuvenated successfully.

In one embodiment, determining 306 may be performed to identify a likely burst pressure, and then to compare it to a threshold. In another embodiment, determining 306 may be performed to verify that an as manufactured minimum burst pressure may be obtained by that vessel (e.g., the design minimum burst pressure). In another embodiment, another minimum burst pressure (e.g., only for the rejuvenation processing purposes) is calculated or compared in the determining 306 step that is equal to the test pressure or an intended autofrettage pressure of the vessel. Various embodiments may be used of this determining step 306 for affirming the ability of the pressure vessel to withstand pressures without significant damage and/or without bursting. As described further herein, these limits for the processing and determining may be adapted as needed.

In one embodiment, determining 306 is performed using a calculation of background energy of the received acoustic information, via averaging a time-window of the information received 304 in response to an increasing of the pressure of the cylinder. This calculation is described further herein with respect to FIG. 4. The calculation of the background energy can identify an internal pressure at which the background energy begins to oscillate. This pressure can be used to calculate a confidence interval for the burst pressure of a vessel in its particular damage state before the vessel is further damaged by the increasing pressure. The calculation of this pressure is described in further detail herein with respect to FIG. 4.

Based on determining 306 to continue pressurizing the vessel, the process continues to increase the internal pressure to the autofrettage pressure. This pressure plastically deforms the plurality of defects in the metallic layer. This plastic deformation has the effect of slowing growth of defects (e.g., depth of defect) during service pressurizations, which weaken the metallic layer causing a shortened life. The depths of defects and the effects of treatment at the autofrettage pressure are described further herein. Also, the autofrettage pressure may not be known for a vessel with an unknown history, and an additional embodiment of a process for the method of determining an appropriate autofrettage pressure for applying to the particular vessel. Specifically, as described further herein, additional information may be analyzed for indication that a sufficient autofrettage pressure has been reached above the test pressure when such threshold is unknown for the vessel prior to processing.

In alternate embodiments, the rejuvenation process 300 may optionally include a delay or holding of the internal pressure at any portion of the process, including at the autofrettage pressure, providing a separation between the increasing of the pressure 302 and 308, and the decreasing of the pressure 310 inside the pressure vessel. As examples, the autofrettage pressure may be held momentarily, or held for an appreciable amount of time. As another example, the autofrettage pressure may be held or adjusted as heat of the pressurizing fluid inside the vessel dissipates. In alternative embodiments, the pressure of the vessel may be varied in addition to simply the described ramps of pressure up to and down from the autofrettage pressure.

After a hold period or after no hold period, the process includes decreasing the internal pressure 310 of the pressure vessel. This process may be monitored, such as via receiving information 312 about the vessel that is created during the decreasing of the pressure. As with other information received herein, the information may be delayed, stored, filtered and/or modified before or after receiving the information 312. Similarly to information received 304 in response to increasing the pressure, in one embodiment, the information received 312 about the vessel in response to decreasing the pressure is specifically originating from the one or more composite layers. In other embodiments, this information also includes information about other portions of the vessel.

The rejuvenation process 300 includes determining 314 that the pressure vessel may receive an additional service interval. This determining 314 may include using any information received about the vessel generated during the process. For example, some information may be received that was generated based on increasing the pressure inside the pressure vessel and other information may be received that was generated based on decreasing the pressure inside the pressure vessel. As another example, information may be received during a hold phase where the pressure is maintained (e.g., shifted up and down about a set point) for a period of time.

In many embodiments, the information is received (e.g., 304, 312) as soon as it is generated by the vessel, or nearly immediately as the information is sensed and transmitted. In other embodiments, the information is delayed or stored before it is received. Determinations based on the information (e.g., 306 and 314) may be made at any time based on the received information. In many embodiments, information received will disqualify the vessel from determining 314 to give vessel additional service interval. In other words, in the majority of embodiments, the process 300 will continue to positive conclusion in the absence of any information that is received and matches certain criteria for disqualifying the vessel. For example, information may be processed when received in steps 304 and/or 312 to make the determination in step 314 whether or not the information will cause the vessel not to receive an additional service interval.

In some embodiments, this determination may be made earlier in the process. In one embodiment, a calculated BEOP under 7500 psi based on data received 304 during increasing the pressure of the pressure vessel may cause the vessel to fail to receive an additional service interval via rejuvenation processing. Thus, the determination 314 may be completed (as failed) as soon as the BEOP is calculated from information received 304, including at a time during the increasing 302 of the pressure, and before continuing 308 to increase the pressure to an autofrettage pressure 308. In one embodiment, based on a counted number of received events (e.g., a counted number of fiber break or delamination events that is under a threshold) in the information received 304 and 312, the process may fail to determine 314 to grant an additional service interval at a time before an autofrettage pressure is reached. For example, the determination 314 may be made (as failed) to the return that particular pressure vessel for an additional service interval as soon as the information is received 304 or 312 and processed enough to make that determination for the particular pressure vessel.

In the absence of such early information indicating sufficient damage, the determination 314 is made that the pressure vessel should receive a new service life interval after the decreasing the pressure 310 is completed (e.g., decreased to ambient pressure). The damage state may increase during processing, and specific determinations (e.g., 306) may be made that continuing to process the vessel will not further damage. For example, a sufficiently high calculated BEOP (FIG. 4) and sufficient modal acoustic emission (MAE) information (e.g., as monitored, stored and/or processed and as described in FIG. 7) may cause the process 300 to make the determination 306 to fail/pass rejuvenation at that point based on an indication of the damage state of the vessel.

Figure 8:
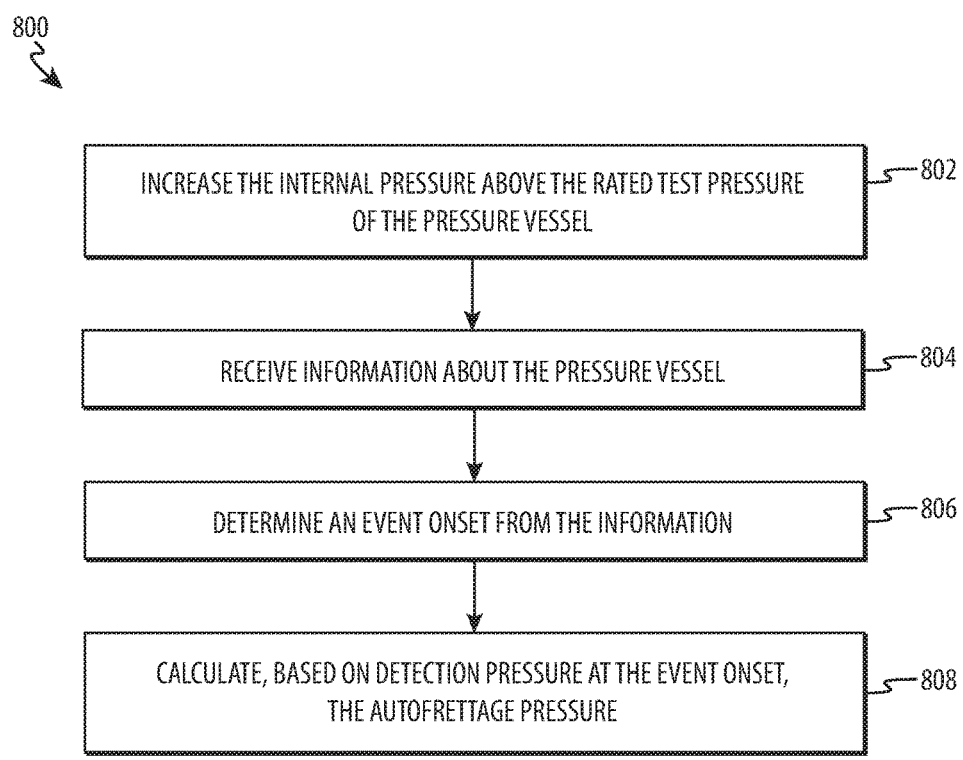
FIG. 8 shows an optional embodiment for rejuvenation processing that includes additional steps for determining an autofrettage pressure for the rejuvenation processing during the process.

In one embodiment, an onset of information received based on a pressure above a test pressure may be used to indicate an autofrettage pressure being reached, as described further herein with respect to FIG. 8.

Several embodiments include storage of information after it is received (304 and 312) and before or during its later use. This storage may be temporary, and only used for calculation purposes. This information storage can include digital or analog storage (e.g., storage of time-based data points, integration of an analog signal) For example, several types of storage may be used to implement the calculations for determining an oscillation in background energy, and to correlate that with a pressure of the pressure vessel, namely a pressure at which that background energy begins to oscillate, or as further described with respect to background energy pressure (BEOP) in FIG. 4.

Storage of information may be further adapted to perform determinations at different times other than in the immediate vicinity of the time when the information was received. For example, the information may be received at one time and the determinations (e.g., 306 and/or 316) based on that information at a later time (e.g., after a further increase or decrease in pressure of the pressure vessel). For example, some of these calculations for determining oscillation of a calculated background energy sensed information require forms of storage, including the calculation of time-window averages of received (sensed) ultrasonic acoustic information.

Figure 4:
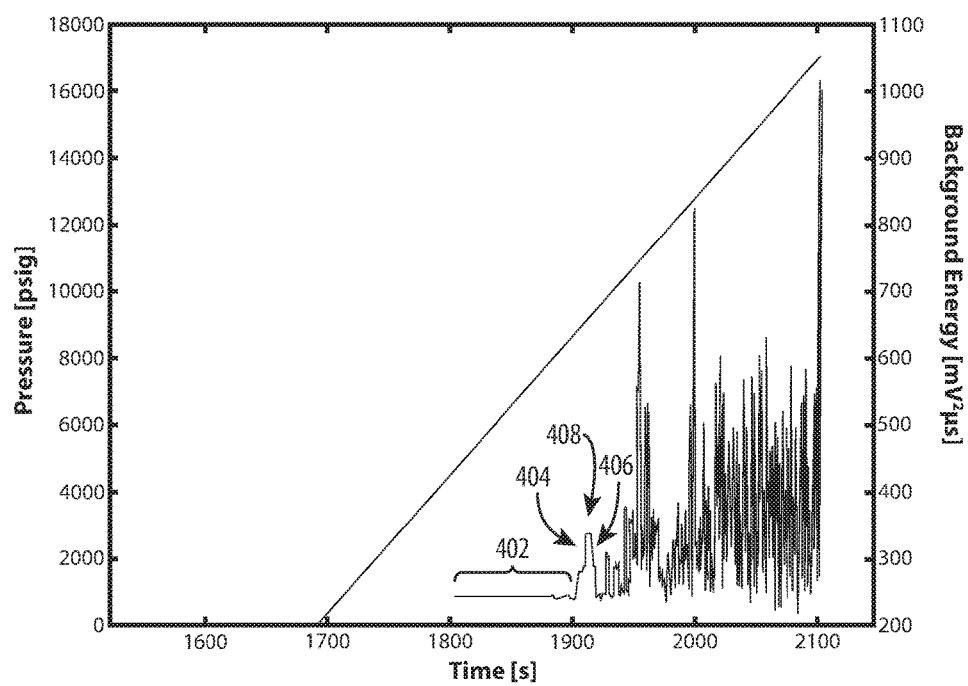
FIG. 4 shows monitored modal acoustic emissions (MAE) for a single cylinder while the cylinder was pressurized in a monotonic increasing of the internal pressure until the ultimate failure of the vessel (e.g., rupture of both of the metallic layer and of the composite layers supporting the metallic layer at the rupture site).

FIG. 4 shows monitored modal acoustic emissions (MAE) for a single cylinder while the cylinder was pressurized in a monotonic increasing of the internal pressure until the ultimate failure of the vessel (e.g., rupture of both of the metallic layer and of the composite layers supporting the metallic layer at the rupture site). The monitored MAE shown are a calculated background energy values which begins at 402 in the lower graph of processed MAE information. This signal begins rising monotonically 404 with the similarly monotonically rising pressure of the vessel. After the rise 404, and due to continued increasing of pressure, the background energy signal peaks at 408 (e.g., exhibits a zero-crossing of the first derivative) and begins to fall 406, in response to increasing internal pressure of the vessel. The background energy signal then begins oscillating after an initial oscillation at 408. The oscillation of this background energy is monitored and associated with an onset or detection pressure at which the information was recorded. This oscillation pressure 408 then ultimately is used (e.g., compared) to another pressure or a threshold to determine information about the damage state of the vessel.

This rise and fall cycle may be filtered (e.g., gated) to only record 408 as an oscillation and not smaller oscillations occurring in 402 that are considered part of the initial information received before initial rise 404 and fall 406, marking an oscillation. In one embodiment, the rise and fall may be mathematically calculated as a zero-crossing of the first derivative after this filtering process is made. In another embodiment, an additional requirement such as an amount of monotonic rise 404 (e.g., within some threshold) before falling 406 is required to determine an oscillation 408 event.

This determined oscillation 408 is an indication of the present damage state of the vessel and the causing of new damage due to the process of increasing of the pressure of the vessel. The oscillation indicates a shift in how the composite layer is redistributing (e.g., allowing for) the increased stresses and strains on the composite layers based on the pressure being held by the metallic layer. The BEOP oscillation pressure determines when the redistribution of internal stresses moves from one mode of supporting the pressure state within the vessel to another mode.

This redistribution of increasing stresses may be represented by a multitude of acoustic emissions from the composite layer. These emissions may include small tremors and larger stronger emissions such as breaks or interfacial failures within the composite layer. The beginning of oscillation of the background energy (e.g., averaged energy of received acoustic information) indicates when significant damage to the vessel begins to occur because the modes of bearing the load shift the monotonic increase in the background information. Thus the energy can be used to indicate the damage of the vessel and this beginning to oscillate can be shown to be consistently linked with the ultimate burst pressure of the vessel under test. Because the background energy includes a moving point average of received information, the time-window of this averaging can be performed and adapted based on experimentation to receive background information that is detected and found to oscillate advantageously as described herein.

This measure of damage by estimating bursting of the vessel is separate measure to fatigue life of the vessel, in which the service damage to the vessel's metallic layer (e.g., cracks, surface wear) grow in depth to the point that the damage causes the metallic layer to fail. Fatigue damage occurs at pressures under or at the test pressure of a vessel, under the repeated pressure cycling and environmental exposure during service. In some embodiments, a minimum burst pressure may be above double the test pressure, thus allowing a vessel to be fatigued during a service interval, and tested for recertification without causing new damage leading to reduced burst pressures (e.g., causing a background energy oscillation, whether monitored or not) or a new characteristic damage state of the vessel.

Figure 5:
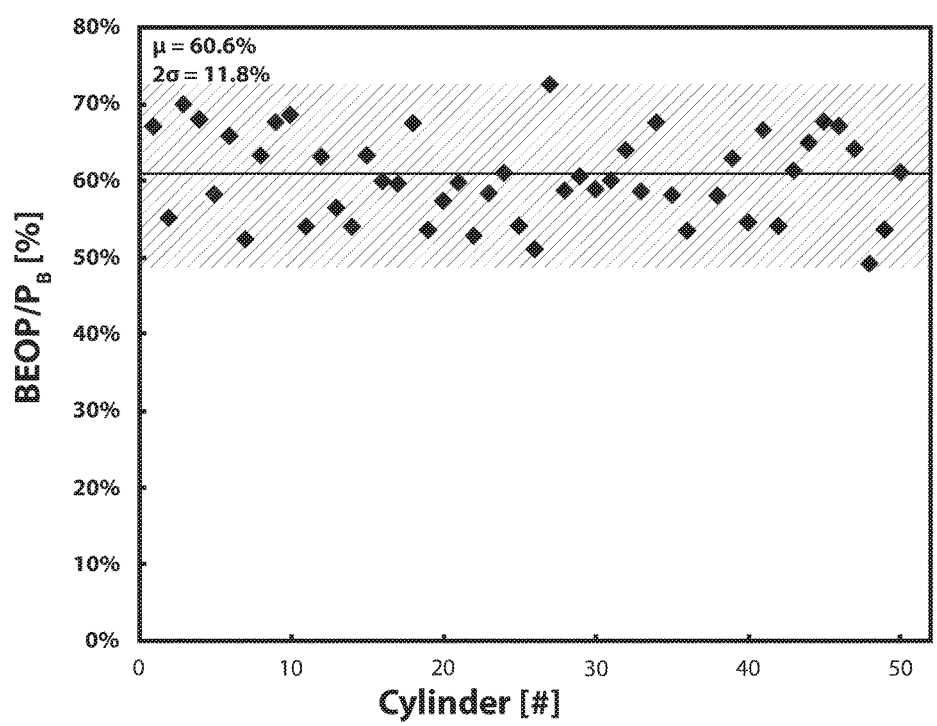
FIG. 5 shows data comparing for fifty cylinders the ratio of the BEOP onset pressure with respect to the final burst pressure (BEOP/PB) for a sample of fifty cylinders that had accumulated unknown levels of damage and were later pressurized to determine BEOP and ultimate burst pressure based on the accumulated damage.

FIG. 5 shows data comparing for fifty cylinders the ratio of the BEOP onset pressure with respect to the final burst pressure (BEOP/PB) for a sample of fifty cylinders that had accumulated unknown levels of damage and were later pressurized to determine BEOP and ultimate burst pressure based on the accumulated damage. The distribution of ratio data shows an average of a BEOP measurement occurring at 60.6 percent of the ultimate burst pressure with a standard deviation of 5.9%. Therefore, the measurement of the onset of background oscillation, based on processed acoustic information demonstrates that monitoring MAE as described herein is an effective predictor of the vessel's ultimate burst pressure.

For example, a determination may be made that a vessel has attained a fraction (e.g., roughly one half, 60%, 60.6%) of the ultimate burst pressure for that vessel based on the oscillation of the calculated background energy received. Because a sensed and calculated background energy oscillation pressure will appear at a fraction (nearly one half) of the ultimate burst pressure, the determination need not be made immediately after sensing and/or calculating the information that would qualify or disqualify such a vessel based on an estimate of the vessel's ultimate burst pressure. In some embodiments, a determination may be delayed that the vessel will or will not meet the required minimum burst pressure for receiving an additional service life interval, and in some embodiments, the determination may be delayed until after the pressurized phases of the rejuvenation processing are completed. In some embodiments, such a determination will be made as part of a determining to continue the pressurizing processes of the rejuvenation process (e.g., increasing the pressure to an autofrettage pressure).

Figure 6:
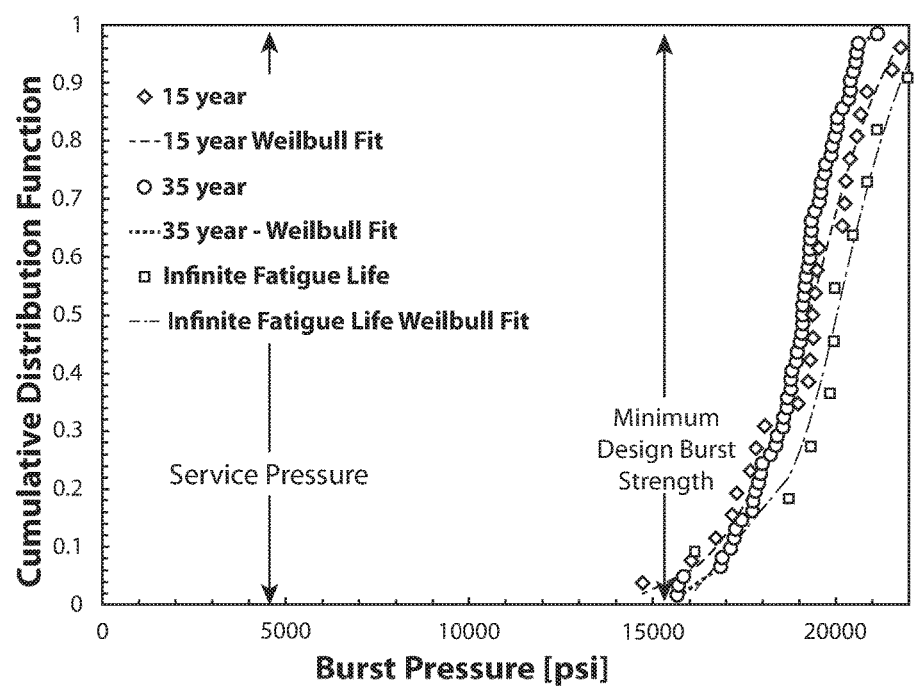
FIG. 6 shows data from eventual burst pressures of three populations of cylinders with different fatigue treatments and including populations that were and were not rejuvenated.

FIG. 6 shows data from eventual burst pressures of three populations of cylinders with different fatigue treatments and including populations that were and were not rejuvenated. The data is shown as the ultimate burst pressure cumulative distributions for each population. The three populations are all populations that were burst after being received with a 15 year actual (i.e., real world) service life. One population was burst as received, ("15 year" data). The other two populations included were treated with the rejuvenation process, with one population receiving 20 years additional simulated service life ("35 year" data), and the other population receiving additional fatigue testing to simulate 48 years of service life (e.g., data shown meeting a threshold for an "infinite fatigue life" rating).

Among the three populations of cylinders that were burst tested, only one cylinder did not attain the minimum burst pressure for newly manufactured cylinders, namely one cylinder from the population that were burst tested in their as-received state. The particular cylinder had already been identified as forewarning a lower burst pressure via information and BEOP measurement showing a predicted lower than sufficient burst pressure.

As shown in the various distributions, simulated service life (e.g., fatigue testing), and routine real world service both have little effect on the eventual demonstrated burst pressure because failure modes for a vessel are often unrelated, such as metallic layer damage (e.g., crack) growth being unrelated to damage in the one or more composite layers. However, real world service can cause unseen and undetected damage to the composite layer(s) that may be only detectable via the monitoring described herein during rejuvenation processing. The determinations, such as for continuing the rejuvenation processing and for granting an additional service interval, may be made based on understandings of these various damage mechanisms and their ability to effect operating parameters for granting that additional service life, including determining that failure by any failure mode will not occur during the granted additional service interval.

In support of these determinations made during the rejuvenation process, the information indicating damage of a vessel may be processed to distinguish the types of damage. For example, information may be received from different parts of the vessel via sensors (e.g., MAE sensors, strain gauges) monitoring the vessel during processing and each of these sets of information may indicate a different type of damage occurring or having occurred to the vessel. As described further herein, the information received from a vessel may be filtered, compared, stored, and/or processed to determine various aspects of the damage in the vessel. These different information may be then used selectively to determine whether the processing should continue and whether it will continue to a successful conclusion of granting the vessel an additional service interval.

Figure 7:
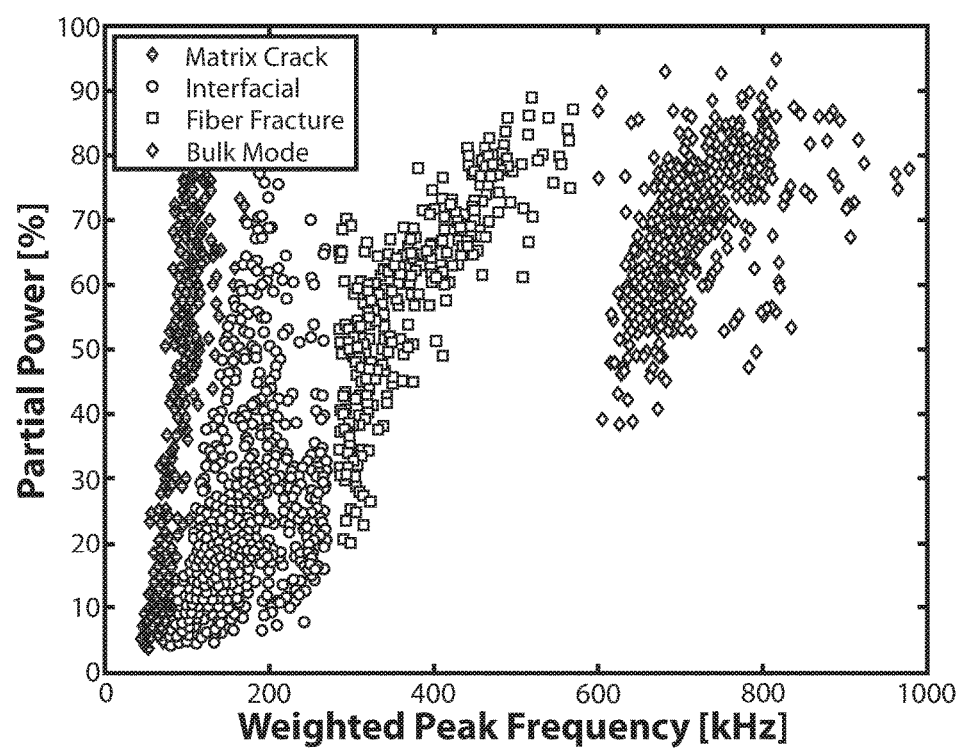
FIG. 7 shows different categorizations of modal acoustic emissions (MAE) received from a vessel while being pressurized during an end of life (EOL) burst test.

FIG. 7 shows different categorizations of modal acoustic emissions (MAE) received from a vessel while being pressurized during an end of life (EOL) burst test. The EOL burst testing includes the creation of many types of damage, creating a widely varying data set from which to study MAE from a vessel in response to damage received. The distributions of the received MAE data are graphed showing the power within a specified frequency band of the received acoustic information plotted against the weighted peak power of the information. The power shown is the partial power of a specified frequency band in the information events, showing the relative dominance of the indicated frequency for the acoustic information received for each event. The exemplary embodiment of EOL burst data shown here are for one vessel, but similar groupings of MAE for damage will occur based on the physical differences in damage mechanisms.

The MAE data are grouped based on weighted peak frequency of the information, demarking the various damage mechanisms that the acoustic information represents as occurring in the vessel. Damage may be generally referred to herein as generally including either fiber breakages (single or bulk mode fractures) and delaminations (matrix cracks or other interfacial damage). For example, as shown in the groupings, matrix cracks in the one or more composite layers are shown in the darkest diamonds at the lowest frequencies, distributed from about 25-100 kHz, depending on the partial power of that information. In other embodiments, frequencies for matrix cracks may be deemed to range from 50-150 kHz, based on the partial power and weighted peak frequency. Other delamination damage (e.g., designated as interfacial damage) to or between the one or more composite layers are shown in moderately lighter diamonds grouped from under 100 kHz (e.g., 75 kHz) up to 250 kHz at lower partial powers. At greater partial powers, interfacial damage produces weighted peak powers at frequencies between 175 kHz and 250 kHz.

The 250 kHz upper limit for interfacial damage appears consistent across a range of partial powers of that weighted peak frequency. Below this threshold, an event may be classified generally as an interfacial failure event, particularly events that do not involve fiber breakage. Alternatively, damage to a vessel via composite fiber fracture (shown in moderately darker diamonds) in the one or more composite layers begins at about 250 kHz across the range of partial powers, indicating that interfacial damage and fiber fracture damage are significantly different damage mechanisms. In the graph, MAE recorded from bulk mode fractures are shown with the highest frequency data points and open diamonds, ranging from 600 kHz to 800 kHz, and in some vessels up to 1,000 kHz (1 MHz).

In several embodiments, distinguishing different damage to vessels can be used to determine whether specific damage criteria have been met, and that determination can cause a further determination whether to grant an additional service interval. For example, one fiber breakage or delamination event recorded during a particular phase of the pressurizing process (e.g., recorded during an increasing pressure phase) may cause a determination that the vessel should not receive an additional service interval. As another example, a combination of events (e.g., a logical combination, a truth table or look up table), may cause a determination and that combination may be bound by a time frame in which the event combination or a portion of the event combination must occur. Such a threshold event combination could be, for example, at least one fiber breakage or delamination event during the increasing pressure phase of the process and at least one delamination event during the decreasing pressure phase of the process.

Based on the physical explanations for these forms of damage, some forms of damage are expected during only the phase(s) of increasing pressure during the process, such as fiber breakage, whereas other forms of damage are expected to possibly occur during several or all phases of the process, such as delaminations (e.g., matrix cracking, interfacial damage). Therefore, in some embodiments, MAE events may be monitored or monitored on for only certain events during some phases and not others. In some embodiments, MAE may be monitored with different categorizations or with blurring of categorizations, or without any regard to some categorizations (e.g., for BEOP averaging calculations). For example, some received acoustic information may be processed to determine whether it represents a likely fiber break or a delamination, or to collect data for BEOP calculation. These events may be recorded as processed or in raw format, such as to perform determinations at later times or to adapt the process at a later time.

FIG. 8 shows an optional embodiment for rejuvenation processing that includes additional steps 800 for determining an autofrettage pressure for the rejuvenation processing during the process. There is various information which may be monitored as part of the processing herein to determine whether or if an autofrettage pressure has been reached, and particularly when an internal pressure of the pressure vessel has plastically yielded the metallic layer and/or plastically yielded portions of the metallic layer around a plurality of defects in the metallic layer.

The autofrettage pressure of a vessel may be unknown for a vessel based on the unknown service history of the vessel. Alternatively, the autofrettage pressure may be unknown for a vessel based on other missing information about the vessel, including a manufacture history of the vessel, or a rejuvenation processing as described herein. In some embodiments, an autofrettage pressure may be presumed or estimated based on the vessel type and a possibly known autofrettage specification at the time of manufacture for that vessel.

In many vessels, the autofrettage pressure at the time of manufacture is around 110%-115% of the test pressure, with a common autofrettage pressure at manufacture set around 112% and around 113%. However, by adding the processing steps 800 to monitor and tailor the rejuvenation processing based on information from the vessel, the entire rejuvenation process can have a limited detrimental effect on the rejuvenated vessel, allowing plasticization of the metallic layer or portions of the layer surrounding the defects to be performed with the minimum damage to the one or more composite layer(s). Therefore, by limiting the damage imparted by the rejuvenation processing, these additional steps 800 may be performed to further extend the service life of a vessel.

The supplementary flow chart shows additional steps 800 for monitoring after increasing the internal pressure 802 above the rated test pressure. In this exemplary embodiment, the process implicitly acknowledges that information containing the indication of the autofrettage pressure having been reached will not be received 804 from the pressure vessel until after surpassing the test pressure. In other embodiments, these assumptions may be changed. For example, an underlying assumption for this exemplary embodiment may include that a manufacturing autofrettage pressure cycle to a pressure above the test pressure (e.g., to 110% test pressure) has been achieved by the vessel before its initial service interval was started. As another example, an underlying assumption for this exemplary embodiment may include that a test pressure cycle is performed periodically during the real world service life of the vessel. As another example, another underlying assumption may be that after entering initial service, no rejuvenation process as described herein has yet been performed.

A rejuvenation process, as described further herein, uses an autofrettage pressure that further plasticizes the metallic layer (or portions thereof) and also may cause additional damage to the vessel (e.g., in the one or more composite layers). Thereafter, the vessel may have a somewhat different (e.g., higher) autofrettage pressure that is necessary to be reached to further plastically strain the metallic layer or portions thereof further. For clarity the term plastic deformation (e.g., plasticize, plastically strain) as used herein with respect to the metallic layer includes straining the metallic layer or a portion of the layer to an extent that the entirety of the strain is not recovered after the internal pressure is lowered (e.g., lowered to equal to the surrounding). Therefore, by monitoring and controlling the increasing pressure process via the additional steps 800, this required additional plastic deformation in the rejuvenation process may include imparting only a small or controlled amount of additional plastic strain on the metallic layer.

The steps 800 of determining the autofrettage pressure include receiving information 804 while the pressure is increased beyond the test pressure. This information may be used to determine 806 an onset of information indicating an autofrettage pressure that will induce plasticization. The information about the onset of plasticization may include only the smallest amount of information needed to calculate or otherwise determine an autofrettage pressure. As described further herein, the calculation 808 of the autofrettage pressure may cause the rejuvenation process to determine that an autofrettage pressure has been reached already inside the vessel and/or is presently pressurizing the vessel (e.g., being maintained in the vessel).

In an exemplary embodiment, the information about the onset of plasticization of a part of the metallic layer can include a strain measurement correlated with an internal pressure increasing the internal pressure 802 that shows that the modulus of the metallic and composite laminate combination shifting to the modulus of only the composite laminate. In this example, strain increases in response to increased stress on the vessel (e.g., internal pressure) resulting at the point of significant plasticization of a different sensed modulus (e.g., lower) of the composite layer(s). In other words, in embodiments where the composite laminate alone provides a lower modulus than the metallic and composite laminate layer combination, the metallic layer or portions thereof can be said to yield within the vessel to the composite layer(s). In this example, strain may be measured to show a shift from a higher modulus measurement to a lower modulus measurement (e.g., shift in strain rate based on a constant stressing or pressurizing rate). Other vessels may exhibit other shifts in strain exhibiting plasticization of the metallic layer.

The strain measurement may be made by placing a strain gauge to measure the straining of the vessel, for example, along a particular orientation of the vessel. A strain gauge orientation may be adapted/selected for monitoring a vessel's onset of plasticization based on the construction shape of the vessel. For example, in the exemplary embodiment of the cylinder-shaped vessel, a hoop-oriented strain gauge may be advantageously used to measure the pressure at which the vessel experiences plasticization of the metallic layer or portions of the metallic layer.

In an alternatively exemplary embodiment, the information received 804 about the onset of plasticization of a part of the metallic layer can include information about increased damage to the one or more composite layers (e.g., further acoustic information received showing additional damage). For example, as described with respect to detecting plasticization directly via strain measurements, continued straining can cause continued damage to the one or more composite layer(s) due to the plasticization of the metallic layer (e.g., yielding of the metallic layer) causing the increasing stresses of pressurization to be held by the composite layer(s). Therefore, monitoring the accumulation of damage beyond the test pressure provides the ability to determine a detection pressure 806 at the onset of MAE information received 804 after the pressure is increased 802 above the test pressure. The detection pressure determined from the onset of the information 806 may be equal to the autofrettage pressure or using some transformation, or estimation. For example, the acoustic information received may be filtered or otherwise pre-processed to provide that the detection pressure is equal to the autofrettage pressure.

The step of calculating the autofrettage pressure 808 may include simply scaling and/or shifting such a detection pressure, such as by equating the pressures, or via some additional information relating the determined 806 detection pressure (e.g., pressure at filtered onset of information). For example, an autofrettage pressure may be determined to be at certain pressure differential (or percentage of the test pressure) over the detection pressure. As described further herein, the rejuvenation process can include the calculated information about the autofrettage pressure to control the timing of the process, such as to stop increasing the pressure of inside the pressure vessel and to start either a hold period or to start decreasing the pressure inside the vessel.

Figure 9:
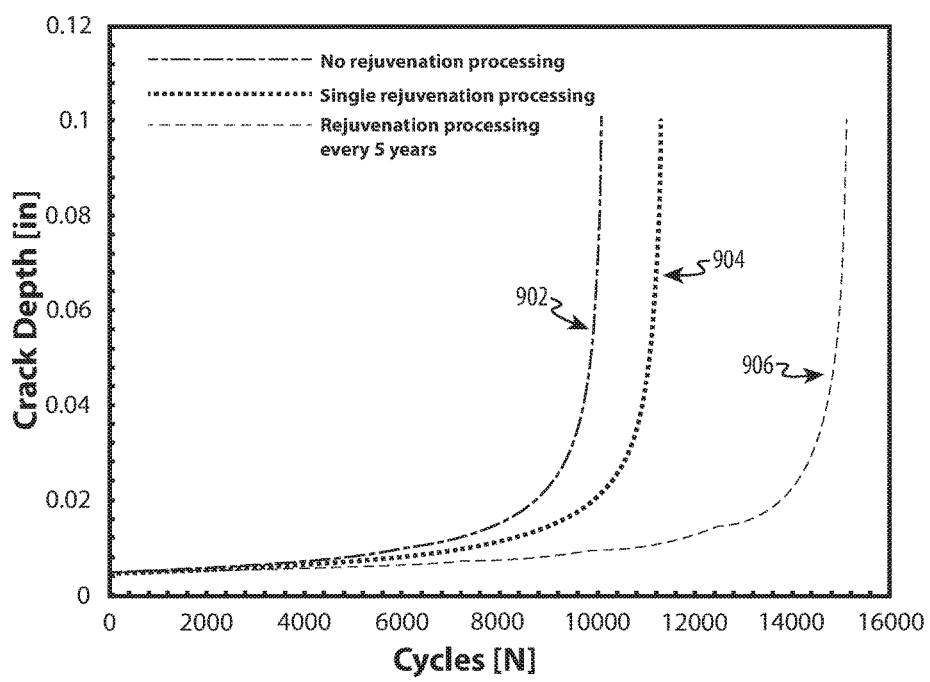
FIG. 9 shows increased fatigue life due to crack growth slowing due to rejuvenation processing and repetition thereof.

FIG. 9 shows increased fatigue life due to crack growth slowing due to rejuvenation processing and repetition thereof. Data are shown for crack growth due to fatigue life cycling due to both a single rejuvenation process (e.g., a re-autofrettage processing of a service expired vessel), and rejuvenation each 5 years of simulated service life (after every 2,500 service cycles). The data illustrates that in each instance an initial crack depth will grow to failure or other leakage of the metallic layer (e.g., at end of vertical graph segments) due to fatigue testing. In some embodiments, rejuvenation processing to an autofrettage pressure may be applied multiple times to a vessel with additional service and recertifications in between successive rejuvenation processes. For example, rejuvenation processing can be performed at the end of a 15 or 20 year service interval, or more frequently, such as each 5 years or 2,500 service pressure cycles. As described further herein, the autofrettage pressure may be known or not known, such as due to a known or unknown pressure history for the vessel, or due to a known or unknown maximum pressure developed in its manufacturing history (e.g., initial autofrettage processing at manufacture) or any previous rejuvenation history.

As shown in the graph, an estimated crack depth of 0.005 in (5 mil) will grow beyond 0.1 in depth (e.g., failure) after a different number of cycles or simulated service life. As shown in the data points representing no rejuvenation processing, the failure period will occur sometime after 10,000 fatigue cycles or 20 years simulated service life. However, with a single rejuvenation process, the service life of a vessel can be safely extended, despite the same initial crack depth, to reach about 11,000 cycles 22 years of simulated service life without further rejuvenation. With additional rejuvenation processes, e.g., every five years, however crack growth may be slowed sufficiently to allow for 15,000 cycles or more (e.g., depending on the repetition of the rejuvenation process) before the crack grows to failure or a simulated life of over 30 more years. In some embodiments, as described further herein, this resistance to fatigue can be used to determine (e.g., qualify) a vessel to receive an "infinite" service life qualification.

Figure 10:
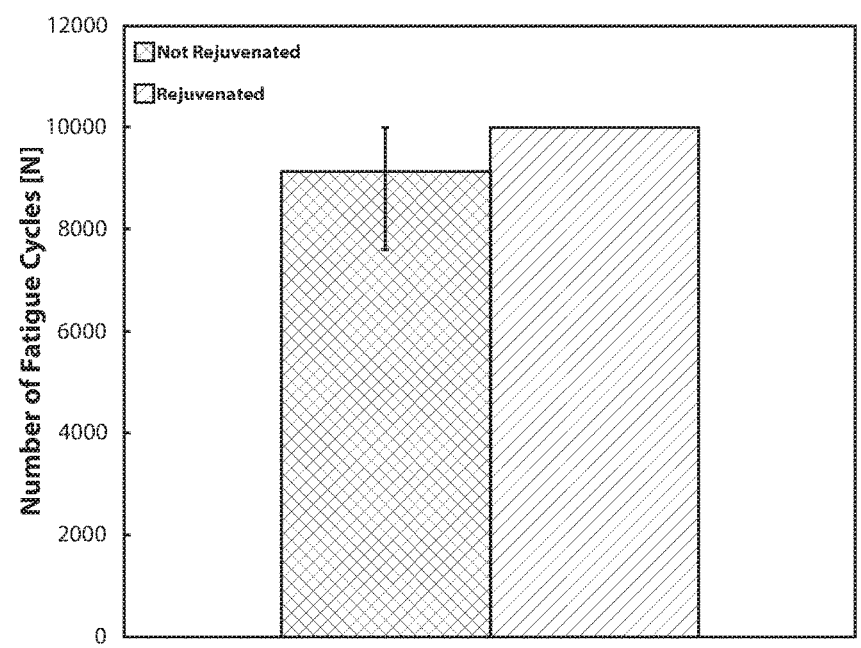
FIG. 10 shows increased fatigue life ability of a population of rejuvenated cylinders versus a population of cylinders that were not rejuvenated after accumulating real world damage during service.

FIG. 10 shows increased fatigue life ability of a population of rejuvenated cylinders versus a population of cylinders that were not rejuvenated after accumulating real-world damage during service. The graph demonstrates pressure cycles to maximum developed pressure after service life until leakage for cylinder populations which were and were not rejuvenated. There were 80 total cylinders received after an initial service interval had expired in real-world service. Half of these cylinders, or forty (40) cylinders were treated with a rejuvenation process as described herein before being fatigue tested to simulate return to service life. The other forty cylinders were fatigue tested with no rejuvenation process applied.

All of the cylinders were then fatigue cycled as described further herein using service pressures and test pressures. The service pressure cycles used herein include cycling between a low pressure and a maximum developed service pressure (e.g., between 400 psi and a fast fill pressure of 5192 psi). Cycles attained were measured as the number of cycles before leakage or other failure, with the intent of achieving a second service life of 20 simulated years, e.g., at least 10,000 fatigue cycles. As described further herein, such a 20 year simulated service life may be presumed to include the simulated test pressure cycles at each of the three interspersed simulated five-year recertifications. Results of testing 80 cylinders in these conditions are shown on the graph with one standard deviation bars also included.

Of the forty (40) cylinders tested that were not rejuvenated, eleven (11) or 27.5% leaked prior to achieving the desired 10,000 fatigue cycles to maximum developed pressure, indicating that only 68.5% of the cylinders were able to withstand the fatigue cycles required for twenty years of extended life service. Conversely, each of the forty (40) cylinders that were rejuvenated prior to fatigue cycle testing achieved the necessary 10,000 fatigue cycles for twenty (20) years of extended service life. Moreover, each of the cylinders that achieved the 10,000 fatigue cycles were later burst at pressures above the initial (manufactured) minimum required burst pressure for these DOT-CFFC cylinders.

Figure 11:
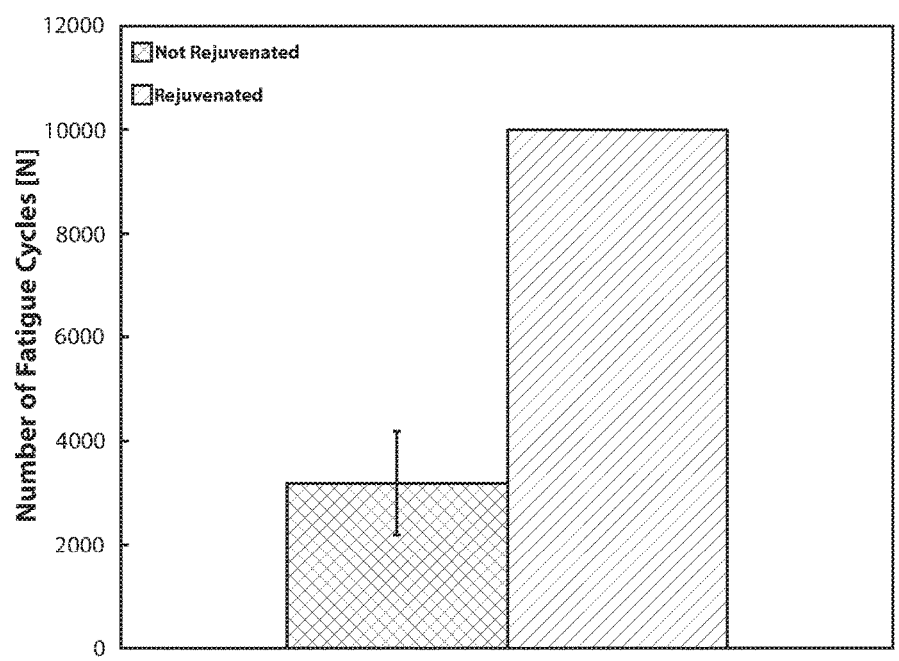
FIG. 11 illustrates the maintained fatigue performance due to rejuvenation treatment of a population of cylinders after additional damage is induced by hard water exposure.

FIG. 11 illustrates the maintained fatigue performance of a population of cylinders after additional damage is induced by hard water exposure due to rejuvenation treatment. The test set up and results are graphed similarly to those in the previous figure, however, in this graph, a hard water treatment (damage) to the inside of the cylinder has been applied to ten (10) cylinders received after their service life has expired. This hard water treatment induces additional defects in the aluminum liner due to interactions with the hard water, such as creating new defects, furthering the depths of other cracks or defects, or creating other weaknesses in the aluminum liner. The hard water treatment was performed to all cylinders before either a rejuvenation process was applied to one half of the population or the cylinders, or five (5) cylinders, while the other half did not receive the rejuvenation process.

The five cylinders that were not rejuvenated were caused to leak at an average of 3,205 cycles, with a standard deviation in the number of cycles to leakage of 1,006. Thus, there is a significant statistical likelihood (e.g., within one standard deviation) that each of these cylinders without rejuvenation treatment would not have survived without leaking for one 5-year requalification interval of a new service life (e.g., 2,500 service cycles).

The additional damage of the hard water treatment illustrates the effects of extreme service environments on the ability to provide an extended service life to a pressure vessel. It also demonstrates the important ability to approve the other cylinders to have any extended service life after being rejuvenation processed as described in detail herein. Each of these cylinders had significantly progressed toward failure after the hard water treatment, over and above the defects that were contained at the end of the service life. Thus, there would be little likelihood that, even if a damaged but not rejuvenated cylinder were to survive an additional 2,500 service pressure cycles, that it could survive a requalification test to achieve another service requalification (e.g., of five years) within the service interval (e.g., of 15 years).

In sharp contrast, the five (5) cylinders which were subjected to the rejuvenation process all obtained 10,000 fatigue cycles to maximum developed pressure (e.g., fast fill pressure) without any leaking, thus demonstrating at least a twenty-year satisfactory service history record. Furthermore, a longer service life may be determined and approved by a safety or regulatory body, including certifying a theoretically indefinite service. For example, this level of certification could be proven by demonstrating 24,000 fatigue cycles (e.g., 48 years of simulated service life) with a test pressure cycle applied during requalification every 2,500 service cycles (e.g., every 5 years of simulated life).

This patent description and drawings are illustrative and are not to be construed as limiting. It is clear that many modifications and variations of this embodiment can be made by one skilled in the art without departing from the spirit of the novel art of this disclosure. While specific parameters, device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. A method, comprising:
receiving a pressure vessel including at least one composite layer and a metallic layer after the pressure vessel has accumulated a plurality of defects in the metallic layer during a first service interval, and the pressure vessel having a rated test pressure;
increasing an internal pressure of the pressure vessel;
receiving first information about the at least one composite layer including at least one modal acoustic emission event that occurs during the increasing the internal pressure of the pressure vessel;
continuing the increasing of the internal pressure of the pressure vessel to an autofrettage pressure that is adapted to plastically strain portions of the metallic layer that are adjacent to each of the plurality of defects;
after the internal pressure reaches the autofrettage pressure, decreasing the internal pressure of the pressure vessel;
receiving second information about the at least one composite layer including at least one modal acoustic emission event that occurs during the decreasing the internal pressure of the pressure vessel;
counting a fiber break event against a predetermined fiber break event threshold for each modal acoustic emission event in the first information with a weighted peak power at a frequency above 250 kHz;
counting a delamination event against a predetermined delamination event threshold for each modal acoustic emission event in either the first information or the second information with a weighted peak power at a frequency below 250 kHz; and
only if the counted fiber break events are under the predetermined fiber break event threshold and only if the counted delamination events are under the predetermined delamination event threshold, then according the pressure vessel an additional service interval beyond the first service interval.

2. The method of claim 1, wherein the counting the delamination event against the predetermined delamination event threshold is performed only if the weighted peak power of the modal acoustic emission event is between 20 and 200 kHz.

3. The method of claim 1, wherein the counting the fiber break event against the predetermined fiber break event threshold is performed only if the weighted peak power of the modal acoustic emission event is between 250 and 800 kHz.

4. The method of claim 1, wherein the fiber break threshold is one and the delamination threshold is more than one.

5. The method of claim 1, wherein the fiber break threshold is one and the delamination threshold is one.

6. The method of claim 1, further comprising:
after increasing the internal pressure above the rated test pressure, receiving third information about at least one modal acoustic emission event indicating damage occurring in the at least one composite layer at a damage detection pressure of the pressure vessel; and
calculating the autofrettage pressure of the pressure vessel based on the damage detection pressure of the pressure vessel.

7. The method of claim 1, further comprising:
after increasing the internal pressure above the rated test pressure, receiving third information about a change in a hoop-oriented strain of the pressure vessel indicating plastic strain in the metallic layer at a plasticization detection pressure of the pressure vessel; and
calculating the autofrettage pressure of the pressure vessel based on the plasticization detection pressure and based on the third information about the event.

8. The method of claim 7, wherein the change in hoop-oriented strain of the pressure vessel indicates damage occurring to the at least one composite layer.

9. The method of claim 1, further comprising:
after increasing the internal pressure of the pressure vessel to the autofrettage pressure, and before decreasing the internal pressure of the pressure vessel below the test pressure;
maintaining the internal pressure of the pressure vessel for a hold period of time; and
receiving hold information including at least one modal acoustic emission event about the pressure vessel occurring during the hold period of time.

10. The method of claim 9, further comprising:
counting based on hold information a fiber break event against the predetermined fiber break event threshold for each modal acoustic emission event in the hold information with a weighted peak power at a frequency above 250 kHz.

11. The method of claim 10, wherein the counting based on hold information the fiber break event against the predetermined fiber break event threshold is performed only if the weighted peak power of the modal acoustic emission event in the hold information is between 250 and 800 kHz.

12. The method of claim 9, further comprising:
counting based on hold information a delamination event against the predetermined delamination event threshold for each modal acoustic emission event in the hold information with a weighted peak power at a frequency below 250 kHz.

13. The method of claim 12, wherein the counting based on hold information the delamination event against the predetermined delamination event threshold is performed only if the weighted peak power of the modal acoustic emission event is between 20 and 200 kHz.

14. A method, comprising:
receiving a pressure vessel including at least one composite layer and a metallic layer, the receiving occurring after the pressure vessel has accumulated a plurality of defects in the metallic layer during a first service interval, and the pressure vessel having a rated test pressure;
increasing an internal pressure of the pressure vessel;
receiving information containing a plurality of modal acoustic emission events from the at least one composite layer occurring during the increasing of the internal pressure of the pressure vessel;
calculating a plurality background energy information from a plurality of moving-averages of the plurality of modal acoustic emission events via averaging energy measurements from a time-windowed selection of the plurality of modal acoustic emission events occurring within a time-window;
based on a zero-crossing of a first derivative in time of the background energy information, counting an oscillation event of the background energy;

correlating the oscillation event with an oscillation pressure of the pressure vessel during the oscillation event; and if the oscillation pressure is less than a threshold percentage of the rated test pressure, then disqualifying the pressure vessel from receiving autofrettage treatment.

15. The method of claim 14, further comprising:

if the oscillation pressure is greater than the threshold percentage of the rated test pressure, then qualifying the pressure vessel for receiving autofrettage treatment.

16. The method of claim 14, wherein the threshold percentage is 50%.

17. The method of claim 14, wherein the threshold percentage is 60%.

* * * * *